(12) United States Patent
Chai et al.

(10) Patent No.: US 9,198,431 B2
(45) Date of Patent: Dec. 1, 2015

(54) USE OF N6-(2-HYDROXYETHYL)-ADENOSINE IN PREPARATION OF CROP PESTICIDE

(71) Applicant: Zhejiang Subtropical Crops Research Institute, Zhejiang Province (CN)

(72) Inventors: Yiqiu Chai, Zhejiang Province (CN);
Guanju Chen, Zhejiang Province (CN);
Yiwei Jin, Zhejiang Province (CN);
Yougao Liu, Zhejiang Province (CN);
Xiaola Li, Zhejiang Province (CN);
Xiangli Dang, Zhejiang Province (CN)

(73) Assignee: Zhejiang Subtropical Crops Research Institute, Zhejiang Province (CN)

( * ) Notice: Subject to any disclaimer, the term of this patent is extended or adjusted under 35 U.S.C. 154(b) by 96 days.

(21) Appl. No.: 14/199,951

(22) Filed: Mar. 6, 2014

(65) Prior Publication Data
US 2014/0256669 A1    Sep. 11, 2014

(30) Foreign Application Priority Data

Mar. 6, 2013 (CN) .......................... 2013 1 0070799

(51) Int. Cl.
*A01N 43/90* (2006.01)
*A01N 43/72* (2006.01)
*A61K 31/7076* (2006.01)

(52) U.S. Cl.
CPC ............... *A01N 43/90* (2013.01); *A01N 43/72* (2013.01); *A61K 31/7076* (2013.01)

(58) Field of Classification Search
None
See application file for complete search history.

(56) References Cited

U.S. PATENT DOCUMENTS 4,783,457 A * 11/1988 Nathanson ................. 514/227.2

* cited by examiner

*Primary Examiner* — Traviss C McIntosh, III
(74) *Attorney, Agent, or Firm* — Osha Liang LLP (57) ABSTRACT

A method for controlling a pest on a crop includes applying a pesticide that comprises N6-(2-hydroxyethyl)-adenosine as an active ingredient for controlling the pest. The pesticide may include 20 wt % N6-(2-hydroxyethyl)-adenosine, 1-3 wt % dispersing agent, and 66.5% wt % water. The pesticide may further include a dispersion agent, a thickening agent, or an antifreeze agent as an auxiliary agent. The dispersing agent may be one or more selected from sodium lignin sulfonate, NNO, Agricultural Emulsifier 500#, Agricultural Emulsifier 700#, Agricultural Emulsifier 600#, Agricultural Emulsifier 1602#, methylene bis-methylnaphthalene sodium sulfonate, sodium salt of alkyl naphthalene sulfonate condensate, or polyoxyethylene castor oil. The thickening agent may be one or more selected from carboxymethyl cellulose, urea, poly vinyl alcohol, aluminum magnesium silicate, or xanthan gum. The antifreeze agent may be one or more selected from ethylene glycol, propylene glycol, glycerol, glycerin-diethylene glycol diethyl ether, methyl-his-propylene glycol, or urea.

14 Claims, 3 Drawing Sheets

USE OF N6-(2-HYDROXYETHYL)-ADENOSINE IN PREPARATION OF CROP PESTICIDE

CROSS REFERENCE TO RELATED APPLICATIONS

The present invention claims priority of Chinese application No. 2013100707997, filed on Mar. 6, 2013, which is hereby incorporated by reference in its entirety including all tables, figures, and claims.

TECHNICAL FIELD

This invention relates to the field of biopesticides, in particular to a pesticide that can be adopted as a pest control measure for crops.

BACKGROUND OF THE INVENTION

A range of issues, such as pesticide hazards and environmental pollution, have attracted people's attention over the years as a result of heavy uses of chemical pesticides and conventional pesticide formulations. Reducing the risks brought by pesticide uses through innovation and improvement of preparation technology, while still pursuing high efficacy, low toxicity and residue, as well as excellent compatibility with the environment, has become a popular issue in the field of pesticide formulations.

Some conventional pesticide formulations, such as powder, wettable powder and emulsifiable concentrate, are gradually replaced by new environmentally friendly water-based formulations, such as suspension concentrates (SC), emulsion in water (EW), suspoemulsion (SE), micro emulsion (ME), water dispersible granule (WG), dry flowable (DF), soluble granules (SG), and capsule suspension (CS). In 1992, the sale volume of suspension concentrates surpassed that of wettable powder and accounted for 23% of the entire pesticide market in the U.K. China started the development of suspension concentrates in 1970s and has gained considerable development in the formulation studies, processing technologies, as well as varieties and quantities. Nonetheless, it's still necessary to provide biopesticides that pose little or no harmful impact on the environment, which should generate little pollution to the nature due to their low residue.

SUMMARY OF THE INVENTION

The present inventors have found that N6-(2-hydroxyethyl)-adenosine, a chemical used in the treatment of certain diseases in medicine, could also be used to effectively kill crop pests.

In one aspect, embodiments of the invention relate to applications of N6-(2-hydroxyethyl)-adenosine in the preparation of crop pesticides. In a preferred embodiment, the pests may be selected from lepidoptera, hymenoptera or homoptera. In some preferred embodiments, the pests are diamondback moths and aphids.

Some embodiments of the invention relates to a pesticide, characterized in that it comprises N6-(2-hydroxyethyl)-adenosine and an auxiliary agent, and that it can be used as pest control on crops.

In preferred embodiments, the pests may be selected from lepidoptera, hymenoptera, or homoptera. In some preferred embodiments, the pests are diamondback moths and aphids.

In preferred embodiments, the auxiliary agents may comprise a dispersing agent, an antifreeze agent, or a thickening agent.

In preferred embodiments, an exemplary pesticide reagent of the invention may comprise 20 wt % of N6-(2-hydroxyethyl)-adenosine, 1-3 wt % of a dispersing agent, and 66.5 wt % of water. In a preferred embodiment, the dispersing agent may be selected from one or more the following reagents: sodium lignin sulfonate, NNO (sodium salt of polynaphthane sulfonic acid), Agricultural Emulsifier 500# (calcium dodecyl benzenesulfonate), Agricultural Emulsifier 700# (octaphenylpolyoxyethlene or OPE), Agricultural Emulsifier 600# (styrylphenol polyoxyethylene ether), Agricultural Emulsifier 1602# (Styrene alkylphenol polyoxyethylene polyoxypropylene ether), methylene bis-methylnaphthalene sodium sulfonate, sodium salt of alkyl naphthalene sulfonate condensate, or polyoxyethylene castor oil. In a preferred embodiment, the dispersing agent may be 3 wt % sodium lignin sulfonate, 2 wt % Agricultural Emulsifier 700#, 1-2 wt % Agricultural Emulsifier 600#, 2 wt % Agricultural Emulsifier 1602#, 1 wt % methylene bis-methylnaphthalene sodium sulfonate, 1 wt % sodium salt of alkyl naphthalene sulfonate condensate, or 1 wt % polyoxyethylene castor oil. In a more preferred embodiment, the dispersing agent may be 3 wt % sodium lignin sulfonate or 1.5 wt % Agricultural Emulsifier 600#.

In a preferred embodiment, the auxiliary agent may be 3 wt % sodium lignin sulfonate, 1.5 wt % Agricultural Emulsifier 600#, 1.5 wt % xanthan gum, 5 wt % glycerol and 3 wt % bentonite.

In a preferred embodiment, the pesticides may exist in one of the following forms, a suspension concentrate, an emulsion in water, a suspoemulsion, a micro emulsion, a water dispersible granule, a dry flowable, a soluble granule, and a capsule suspension. In addition, the pesticides prepared may exist in a combination of the above-described forms.

In preferred embodiments, the thickening agent may be carboxymethyl cellulose, urea, poly vinyl alcohol, aluminum magnesium silicate, or xanthan gum.

In preferred embodiments, the auxiliary agent may also contain an antifreeze agent, which is one or more selected from ethylene glycol, propylene glycol, glycerol, glycerindiethylene glycol diethyl ether, methyl-bis-propylene glycol, or urea.

One skilled in the art would know that pesticides can be prepared with selected concentrations of N6-(2-hydroxyethyl)-adenosine as needed. For instance, its concentration can vary from about 1-50%. The pesticide can be obtained using 5 wt %, 20 wt %, 25 wt % and 30 wt % concentration series of N6-(2-hydroxyethyl)-adenosine.

The active ingredient of this invention, N6-(2-hydroxyethyl)-adenosine, can be separated from naturally existing substances through extraction or purchased in the commercial market. For example, it can be extracted as per the method described in Chinese Patent 200610008465.7 or purchased from Shanghai Xinran Science & Technology Development Co., Ltd (Address: Room 501, No. 1 Lane 35, Shenbang Road, Shanghai). The substance is usually used as medicine in pharmaceutical fields, such as research in pain killers. The inventors of the present invention found that this chemical also has lethal effects on certain crop pests, and, therefore, it can be used as a pest control reagent.

BENEFICIAL EFFECTS

This invention provides a new biopesticide, one that is made with raw materials that are easy to get and prepare while producing little pollution to the environment, thereby being bound to be a competitive and promising force in the market.

DETAILED DESCRIPTION OF THE INVENTION

Embodiments of the invention relate to pesticides that comprise N6-(2-hydroxyethyl)-adenosine as a pest control ingredient, and methods of using such pesticides to control pests on crops. N6-(2-hydroxyethyl)-adenosine is a known chemical that has been used in pharmaceutical and other fields. As noted above, use of N6-(2-hydroxyethyl)-adenosine as a pesticide would have less undesirable impact on the environment.

Embodiments of the invention would be illustrated with the following examples. One skilled in the art would appreciate that these examples are for illustration only and are not intended to limit the scope of the invention because modifications and variations are possible without departing from the scope of the invention.

EXAMPLES

Example 1

Preparation of Suspending Agent Containing N6-(2-Hydroxyethyl)-Adenosine

Materials

Reagents used in the examples can be obtained from any commercial sources. The following are examples: N6-(2-Hydroxyethyl)-Adenosine (≥98%) (from Shanghai Xinran Science & Technology Development Co., Ltd (Address: Room 501, No. 1 Lane 35, Shenbang Road, Shanghai)); Sodium Lignin Sulfonate (Russia), Guangzhou Baiyan Chemicals Co., Ltd.; sodium salt of polynaphthalene sulfonic acid (NNO), Shanghai Auxiliaries; Agricultural Emulsifier 500#, 700#, 600# and 1602#, Xingtai Lanxing Auxiliary Factory; methylene bis-methylnaphthalene sodium sulfonate (MF), Shanghai Auxiliaries; sodium salt of alkyl naphthalene sulfonate condensate (M), AKZO NOBEL Co.; Polyoxyethylene Castor Oil (BY), Oster Chemicals Ltd.; Xanthan Gum (XG), Zibo Hailan Chemical Co., Ltd.; Glycerol, Shanghai Auxiliaries; Bentonite, Weifang Fangzi District Xinglong Bentonite.

Instrument and Equipment

The instrument and equipment in these examples are as follows: Shimadzu LC-6A High Performance Liquid Chromatography from Japan; S-501 Ultra-Digital Thermostat (Liaoyang Boda Scientific Instrument Ltd.); DNP-9162 Electro-Thermal Incubator (Shanghai Jing Hong Laboratory Instrument Co., Ltd.); NDJ Rotating Viscosimeter (Shanghai Balance); Malvern Laser Particle Size Distribution Analyzer (Malvern Instruments Ltd.); High Shear Mixing Emulsifier (Shanghai Kunfeng Daily Chemical Ltd.); Sand Mill (Shenyang Research Institute of Chemical Industries).

Embodiment 1

Preparation of Suspensions

Figure 1:
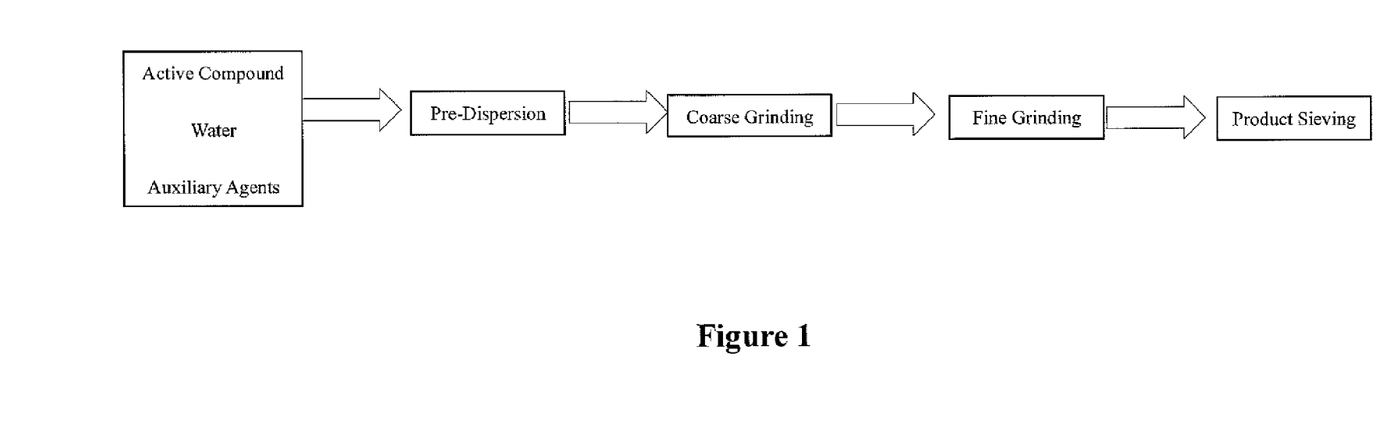
FIG. 1 shows a flowchart illustrating a process for the preparation of 20% paecilomyces cicadae (N6-(2-hydroxyethyl)-adenosine) extract suspension in accordance with a preferred embodiment of the invention.

Weigh the raw materials (including the active ingredient N6-(2-hydroxyethyl)-adenosine, a dispersing agent, an antifreeze agent, a thickening agent, and water) out and put them in a mixing tank as specified by the formulation. Turn on the high shear emulsifier and stir the materials at the speed of 9000r/min for 5 min. After coarse grinding, transfer the paste into a sand mill and start sanding until the grains are 3-5 μm in diameter on average, when the product is finished. An exemplary process flow is shown in FIG. 1.

Example 2

Selection of Wetting Dispersing Agent

A suspension concentrate is an unstable dispersed system with grains of only several micrometers in diameters suspended in a liquid. If the dispersing agent selected is not compatible with the physiochemical properties of the active ingredient, N6-(2-hydroxyethyl)-adenosine, the poor stability of the resulting suspension concentrate will eventually lead to precipitation and build-up of grains or particulates in storage, which would impair the quality and efficacy of the products. After extensive preliminary work and careful screening, together with the research experiences in the physiochemical properties of N6-(2-hydroxyethyl)-adenosine, a variety of dispersing agents, including sodium lignin sulfonate, NNO, 500#, 700#, 600#, 1602#, MF, M and BY, were selected for testing. The experimental results (see Table 1) indicate that the formulations of Samples No. 1 and No. 2 did not meet the specifications for pesticide suspension concentrate, whereas those of Samples No. 3-10 all met the requirements, among which Sample No. 6 showed the best stability and efficacy.

TABLE 1

Formulation Screening of Suspending Agent Prepared with 20% N6-(2-Hydroxyethyl)-Adenosine

| Formula | 1 | 2 | 3 | 4 | 5 | 6 | 7 | 8 | 9 | 10 |
|---|---|---|---|---|---|---|---|---|---|---|
| N6-(2-Hydroxyethyl)-Adenosine (%) | 20.5 | 20.5 | 20.5 | 20.5 | 20.5 | 20.5 | 20.5 | 20.5 | 20.5 | 20.5 |
| Sodium Lignin Sulfonate (%) | 3 | 3 | 3 | 3 | 3 | 3 | 3 | 3 | 3 | 3 |
| NNO (%) | 2 | | | | | | | | | |

TABLE 1-continued

Formulation Screening of Suspending Agent Prepared with 20% N6-(2-Hydroxyethyl)-Adenosine

| Formula | 1 | 2 | 3 | 4 | 5 | 6 | 7 | 8 | 9 | 10 |
|---|---|---|---|---|---|---|---|---|---|---|
| 500# (%) |  | 2 |  |  |  |  |  |  |  |  |
| 700# (%) |  |  | 2 |  |  |  |  |  |  |  |
| 600# (%) |  |  |  | 2 | 1 | 1.5 | 1 |  |  |  |
| 1602# (%) |  |  |  |  |  |  |  | 2 |  |  |
| MF (%) |  |  |  |  |  |  |  |  | 1 |  |
| M (%) |  |  |  |  | 1 |  |  |  |  | 1 |
| BY (%) |  |  |  |  |  |  | 1 |  |  |  |
| Xanthan Gum (%) |  |  |  |  |  | 1.5 |  |  | 3 | 3 |
| Glycerol (%) | 5 | 5 | 5 | 5 | 5 | 5 | 5 | 5 | 5 | 5 |
| Bentonite (%) | 3 | 3 | 3 | 3 | 3 | 3 | 3 | 3 | 3 | 3 |
| Water (%) | 66.5 | 66.5 | 66.5 | 66.5 | 66.5 | 65.5 | 66.5 | 66.5 | 64.5 | 64.5 |
| Suspension Rate (%) | 87.2 | 65.8 | 89.5 | 92.8 | 93.4 | 99.6 | 96.5 | 90.5 | 98.5 | 97.2 |
| Sieving Rate (%) | 96 | 92 | 99 | 99 | 99 | 99 | 99 | 99 | 99 | 99 |
| Dispersity | Good | Fair | Good | Good | Good | Good | Good | Good | Good | Good |
| Cold Storage Stability | Good − | Good | Good | Good | Good | Good + | Good | Good − | Good + | Good + |
| Hot Storage Stability | Poor | Poor | Fair | Fair | Fair | Good | Good | Fair | Good | Good |

Example 3

Selection of Thickening Agent

Viscosity is one of the 3 key factors that affect the stability of a suspension concentrate. Moderate viscosity will give the reagent an excellent stability and a high suspension rate. In our experiments, we used xanthan gum, carboxymethyl cellulose, urea, poly vinyl alcohol, and aluminum magnesium silicate, which are the usual choices of thickening agents.

Moderate viscosity can be obtained by using xanthan gum as s thickening agent. However, 3% or more of xanthan gum will create too high a viscosity and affect the product's dispersability and suspension rate in water. Therefore, embodiments of the invention preferably use less than 3% of xanthan gum. For example, 1.5% xanthan gum will generate a desired viscosity without affecting the dispersity and suspension rate of the product (refer to Table 1 for experimental data of each formulation).

Example 4

Selection of Antifreeze Agent

Antifreeze agents are also known as freezing-point conditioners or anticoagulants. For pesticide suspension concentrates relying on water as its dispersing medium, not only does its formulation has to be suitable for the product's manufacturing, storage and application in the south, but also it has to be equally suitable to stand the cold weather in the north. Addition of an antifreeze agent may be reduced or optional for applications in the south; however, addition of an antifreeze may be necessary for applications in the north. Antifreeze agents for use with embodiments of this invention may include ethylene glycol, propylene glycol, glycerol, glycerin-diethylene glycol diethyl ether, methyl-bis-propylene glycol, and urea. Ethylene glycol, urea, and glycerol were selected in the formulations for testing their antifreeze effects. According to the results, desired effects could be achieved, for example, by using 5% glycerol, which kept the product from becoming frozen after storage at −18° C. for 7 days (refer to Table 1 for experimental data of each formulation).

Example 5

Hot Storage Stability Test

To test the thermal stability of the formulations, a sample (Formulation No. 6) was put in an ampoule bottle and the bottle was sealed and put in a thermostat oven set to 54±2° C. After 14 days in hot storage, the sample was removed from the oven for test and analysis. The test results indicated that a range of indexes of the 20% N6-(2-hydroxyethyl)-adenosine suspension, including the decomposition rate of active ingredient, suspension rate, fluidity, pourability and wet sieving rate, were all up to the standards (refer to Table 1 for experimental data of each formulation).

Example 6

Determination of Various Technical Indices of a 20% N6-(2-Hydroxyethyl)-Adenosine Suspension Tests on various technical indexes of the sample prepared as per above-mentioned Formulation No. 6 (Example 5) were carried out and the results are shown in Table 2 below.

TABLE 2

Test Results of Various Technical Indices of a 20% N6-(2-Hydroxyethyl)-Adenosine Suspension

| Item | Test Result |
|---|---|
| Mass Fraction of N6-(2-Hydroxyethyl)-Adenosine (%) | 20.1 |
| pH | 6.3 |
| Suspension Rate | 99.4 |
| Pourability Post-Pouring Residue (%) | 3.8 |
| Post-Washing Residue (%) | 0.2 |
| Wet Sieving Test (Getting Through 75 μm Test Sieve) (%) | 99 |
| Foaming Persistence (after 1 min)/ml | 20 |
| Low Temperature Stability | Pass |
| Hot Storage Stability | Pass |

Example 7

Indoor Bioassay Test

Indoor bioassay tests were carried out on diamondback moths using a reagent prepared as per Formulation No. 6. 96 hours after the treatment, the average corrected death rates of the 500 mg/L, 400 mg/L, 300 mg/L, 200 mg/L, and 100 mg/L treatment groups were 86.84%, 84.21%, 68.42%, 32.89%, and 27.63%, respectively, as shown in Table 3 The average corrected death rate of the 500 mg/L treatment group was significantly higher than that of the 300 mg/L, 200 mg/L, or 100 mg/L group (P<0.01), while no significant difference was found between the 500 mg/L and 400 mg/L groups. The average corrected death rate of the 400 mg/L treatment group was significantly higher than that of the 300 mg/L group (P<0.05) and significantly higher than that of the 200 mg/L and 100 mg/L groups (P<0.01). There was no significant difference between the average corrected death rates of the 200 mg/L and 100 mg/L treatment groups.

TABLE 3

Pest Control Efficacy of a 20% N6-(2-Hydroxyethyl)-Adenosine Suspension on Diamondback Moth

| CONCEN-TRATION (mg/L) | AVERAGE CORRECTED DEATH RATE (%) | | | |
|---|---|---|---|---|
| | 24 h | 48 h | 72 h | 96 h |
| 500 | 30.00 aA | 53.75 aA | 78.21 aA | 86.84 aA |
| 400 | 25.00 aA | 48.75 aA | 71.79 aAB | 84.21 aAB |
| 300 | 16.25 bB | 35.00 bB | 58.97 bB | 68.42 bB |
| 200 | 7.50 cC | 13.75 cC | 28.21 cC | 32.89 cC |
| 100 | 6.25 cC | 8.75 cC | 21.79 cC | 27.63 cC |

Similar results were obtained from similar experiments carried out with samples prepared according to Formulations No. 3-5, 7-10 (experimental data omitted).

CONCLUSIONS

Results from indoor bioassay test on a 20% N6-(2-hydroxyethyl)-adenosine suspension prepared according to the formulations indicated that the 400 mg/L treatment group had a 96-hour average corrected death rate of over 80%, which provides a high insecticidal efficacy on diamondback moth. Not only is the 20% N6-(2-hydroxyethyl)-adenosine suspension characterized with its simple production process, reliable efficacy and credible quality, but it is also made with raw materials that are easy to obtain and prepare, while producing very little pollution to the environment. Thus, these pesticides will be a competitive and promising force in the market.

Example 8

Role of N6-(2-Hydroxyethyl)-Adenosine in the Insecticidal Activity of Diamondback Moth

Tested Materials

Test Reagent: 20% N6-(2-hydroxyethyl)-adenosine suspension (Formulation No. 6 in Example 1).
Test Insects: Artificial subculture breeding of diamondback moths collected at Xinqiao greenhouse vegetable field in Wenzhou was carried out in a thermostat illumination incubator and the second-instar larvae breeds of a consistent size and color were picked for tests.

Test Method:
Preparing N6-(2-hydroxyethyl)-adenosine solutions of various concentrations;
Diluting the 20% N6-(2-hydroxyethyl)-adenosine suspension to make solutions with 1000 mg/L, 800 mg/L, 600 mg/L, 400 mg/L, and 200 mg/L active ingredient concentrations, respectively, for testing the roles of N6-(2-hydroxyethyl)-adenosine in stomach poisoning of diamondback moth larvae.
Diluting the 20% N6-(2-hydroxyethyl)-adenosine suspending agent to make solutions with 300 mg/L, 250 mg/L, 200 mg/L, 150 mg/L and 100 mg/L active ingredient concentrations, respectively, to test the roles of N6-(2-hydroxyethyl)-adenosine in suppressing feeding and retarding development of diamondback moth larvae.

Treatment of Tested Larvae

Determination of the Role N6-(2-Hydroxyethyl)-Adenosine Plays in the Oral Toxicity of Diamondback Moth Larvae Cut healthy, fresh cabbage leaves in small pieces that are 7 cm in diameters. Smear these pieces with various spore suspensions and leave them to dry naturally. Repeat the smearing process 3 times, and then put the leaves in plastic Petri-dishes with tiny holes that are 2 cm in diameter. Cover the dishes with nylon membranes to keep the leaves fresh.
Pick out healthy indoor bred third-instar diamondback moth larvae of similar sizes with a writing brush, and inoculate them onto the cabbage leaves. Make 4 replicas of the treatments, each of which should contain 20 tested larvae. Cultivate the dishes in an incubator set to 25±1° C., 75~80% relative humidity and 16 L:8D illumination. Observe and record the number of larvae that die of infection every day. Use 0.1% triton solution as a blank control and use the Abbott formula for correction of death rates. Corrected Death Rate (%)=[(Death Rate of the Treatment Group−Death Rate of the Control Group)/(1−Death Rate of the Control Group)]×100.

Determination of the Role N6-(2-Hydroxyethyl)-Adenosine in Antifeeding of Diamondback Moth Larvae Round leaf disk dipping method was employed in this test. Prepare leaf disks out of cabbage leaves with a round hole puncher (d=2 cm), and soak the disks in N6-(2-hydroxyethyl)-adenosine solutions with different concentrations for 30 seconds. Then, take the leaf disks out and drain the excessive solution with clean blotting paper to prepare them for treatments. Use 0.1% triton solution as a blank control.

Selective Antifeeding (Feeding Suppression) Effects

Put a good-size piece of filter paper in a Petri-dish, and then put two processed and two control leaf disks into the same Petri-dish, which are arrayed in a cross fashion. Inoculate three third-instar diamondback moth larvae that have been subjected to 4-hour starvation treatments onto the leaf disks and seal the dish. Prepare 10 replicas for each treatment group. After 48 hours, pick five replicas with 0% death rate to measure the leaf areas that have been consumed by the larvae with a grid paper and calculate the average leaf consumption areas.

Antifeeding Rate (%)=[(Leaf Consumption Area in the Control Group−Leaf Consumption Area in the Treatment Group)÷(Leaf Consumption Area in the Control Group+Leaf Consumption Area in the Treatment Group)]×100.

Non-Selective Antifeeding Effects

Put a good-sized piece of filter paper in a Petri-dish, and then put two processed leaf disks in the same Petri-dish and another two control leaf disks in a different dish. Inoculate three third-instar diamondback moth larvae that have been subjected to 4-hour starvation treatments onto the leaf disks and seal the dish. Prepare 10 replicas for each treatment group. After 48 hours, pick five replicas with 0% death rate to measure the leaf areas that have been consumed by the larvae with a grid paper and calculate the average leaf consumption areas.

Non-Selective Antifeeding Rate (%)=[(Leaf Consumption Area in the Control Group—Leaf Consumption Area in the Treatment Group)÷Leaf Consumption Area in the Control Group]×100.

Determination of the Role
N6-(2-Hydroxyethyl)-Adenosine in the Development Retardation of Diamondback Moth Larvae Soak the cabbage leaves (7 cm in diameters) in the prepared solutions for 30 seconds, take the leaves out, leave them to dry, and then transfer the dried leaves to a Petri-dish (9 cm in diameter) cushioned with a wet filter paper. Inoculate 15 weighed third-instar diamondback moth larvae onto each Petri-dish. After 3 days, pick out 10 survived larvae and have them weighted again. Prepare four replicas for each treatment group to determine the effects of various solutions in inhibiting the weight gain of the larvae.

Weight-Gain Inhibition Rate (%)=[(the Average Weight Gain of the Control Group–the Average Weight Gain of the Treatment Group)÷the Average Weight Gain of the Control Group]×100.

Data Analysis

The results obtained were analyzed for significances of difference using Ducan's New Multiple Range Method. The various lowercase letters following the data in the same column indicate significant differences at a level of 0.05 level (P<0.05). The various capital letters following the data in the same column indicate significant differences at a level of 0.01 (P<0.01).

Results and Analysis

Stomach Poisoning Effects of
N6-(2-Hydroxyethyl)-Adenosine Suspension on Diamondback Moth Table 4 shows that treatment groups of 1000 mg/L, 800 mg/L, 600 mg/L, 400 mg/L and 200 mg/L of N6-(2-hydroxyethyl)-adenosine. All had certain stomach poisoning effects on diamondback moths, and the average corrected death rates of the moths increased with the solution concentrations. Even though the 25-hour post-treatment death rates of the larvae at various concentrations were below 30%, the tested larvae all showed loss of appetite and energy, as well as sluggishness in response to the treatments. On top of that, these symptoms appeared to become more obvious as the concentrations of the solutions increase.

Forty-eight (48) hours after the treatment, the average corrected death rates of the 1000 mg/L and 800 mg/L tested groups were 53.75% and 48.75%, respectively. It is clear that there was no significant difference between the rates of these two groups, and both had significantly higher rates than those of the 600 mg/L, 400 mg/L and 200 mg/L groups (P<0.01). The average corrected death rate of the 600 mg/L group was remarkably higher than that of the 400 mg/L and 200 mg/L groups (P<0.01). There was no significant difference between the average corrected death rates of the 400 mg/L and 200 mg/L groups.

Seventy-two (72) hours after the treatment, the average corrected death rates of the 1000 mg/L, 800 mg/L, 600 mg/L, 400 mg/L and 200 mg/L tested groups were 78.21%, 71.79%, 58.97%, 28.21% and 21.79%, respectively. The 1000 mg/L group had an average corrected death rate that was notably higher than that of the 600 mg/L, 400 mg/L and 200 mg/L groups (P<0.01). However, the average corrected death rate of the 1000 mg/L group had no significant difference as compared to that of the 800 mg/L group. The average corrected death rate of the 800 mg/L group was significantly higher than that of the 600 mg/L group (P<0.05) and remarkably higher as compared with those of the 400 mg/L and 200 mg/L groups (P<0.01). Significant difference was not observed between the average corrected death rates of the 400 mg/L and 200 mg/L groups.

Ninety-six (96) hours after the treatment, the average corrected death rates of the 1000 mg/L, 800 mg/L, 600 mg/L, 400 mg/L and 200 mg/L tested groups were 86.84%, 71.79%, 84.21%, 68.42% and 32.89%, respectively. The 1000 mg/L group had an average corrected death rate that was notably higher than those of the 600 mg/L, 400 mg/L and 200 mg/L groups (P<0.01). However, the average corrected death rate of the 1000 mg/L group was not significantly different, as compared to that of the 800 mg/L group. The average corrected death rate of the 800 mg/L group was significantly higher than that of the 600 mg/L group (P<0.05) and remarkably higher than those of the 400 mg/L and 200 mg/L groups (P<0.01). Significant difference was not observed between the average corrected death rates of the 400 mg/L and 200 mg/L groups.

TABLE 4

Stomach Poisoning Effects of N6-(2-Hydroxyethyl)-Adenosine Suspension on Diamondback Moth

| Concentration | Average Corrected Death Rate (%) | | | |
|---|---|---|---|---|
| (mg/L) | 24 h | 48 h | 72 h | 96 h |
| 1000 | 30.00 aA | 53.75 aA | 78.21 aA | 86.84 aA |
| 800 | 25.00 aA | 48.75 aA | 71.79 aAB | 84.21 aAB |
| 600 | 16.25 bB | 35.00 bB | 58.97 bB | 68.42 bB |
| 400 | 7.50 cC | 13.75 cC | 28.21 cC | 32.89 cC |
| 200 | 6.25 cC | 8.75 cC | 21.79 cC | 27.63 cC |

Antifeeding Effects of
N6-(2-Hydroxyethyl)-Adenosine Suspension on Diamondback Moth Results from indoor antifeeding activity tests (FIGS. 2 and 3) indicate that the tested larvae showed clear declines in their feeding capacity after being treated with 300 mg/L, 250 mg/L, 200 mg/L, 150 mg/L and 100 mg/L of N6-(2-hydroxyethyl)-adenosine (prepared using a 20% suspension), These results suggest that the solutions had certain antifeeding effects on the third-instar diamondback moth larvae, wherein the antifeeding activity increased with increasing concentrations of the solutions.

Figure 2:
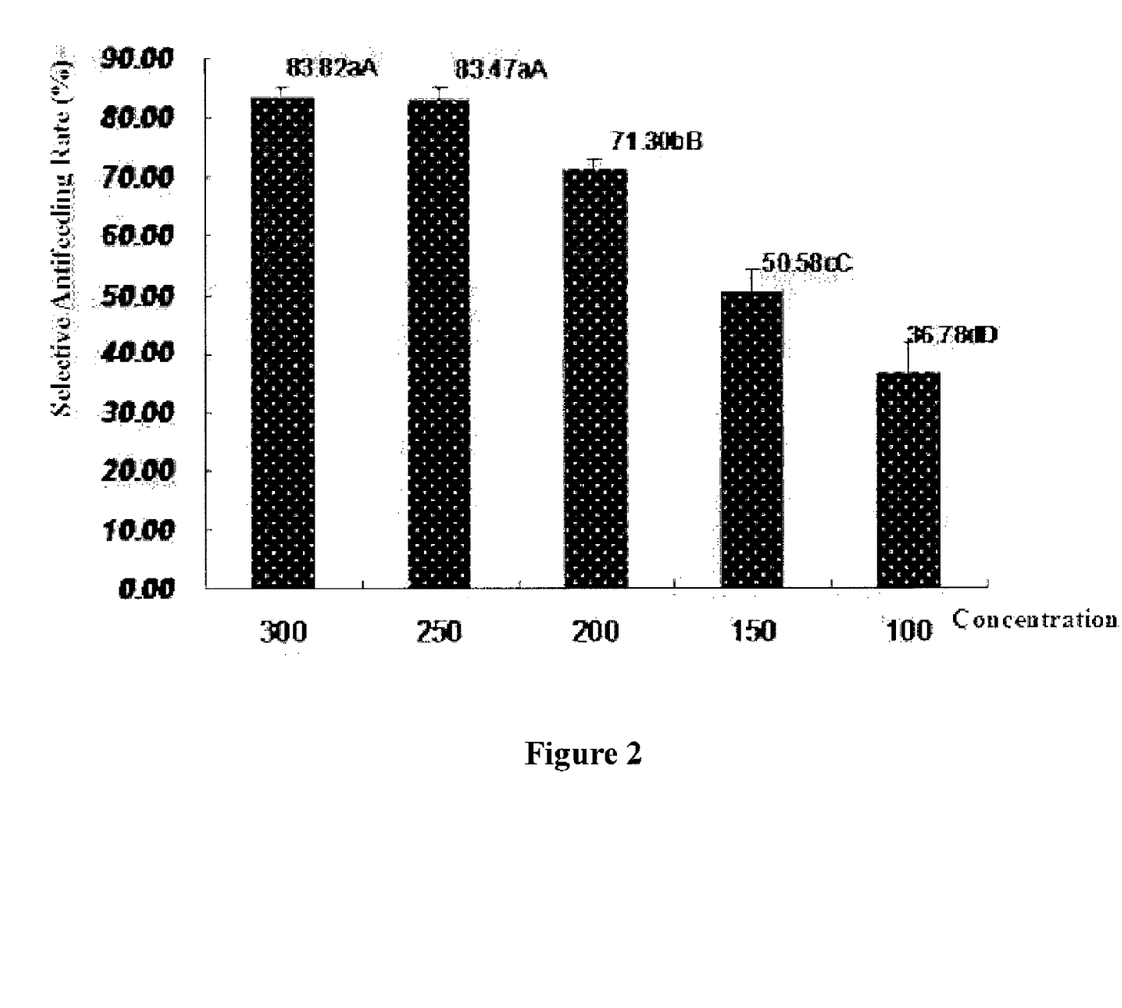
FIG. 2 shows selective antifeeding (feeding suppression) effects of N6-(2-hydroxyethyl)-adenosine on diamondback moth.

Forty-eight (48) hours after the treatment, the selective antifeeding rates of the larvae tested with 300 mg/L and 250 mg/L of N6-(2-hydroxyethyl)-adenosine (prepared using a 20% suspension) were 83.82% and 83.47%, respectively, indicating that there was no significant difference between the selective antifeeding rates of these two groups. However, the selective antifeeeding rates of both these groups were notably higher than those of the groups treated with lower concentrations of the solutions (P<0.01).

Figure 3:
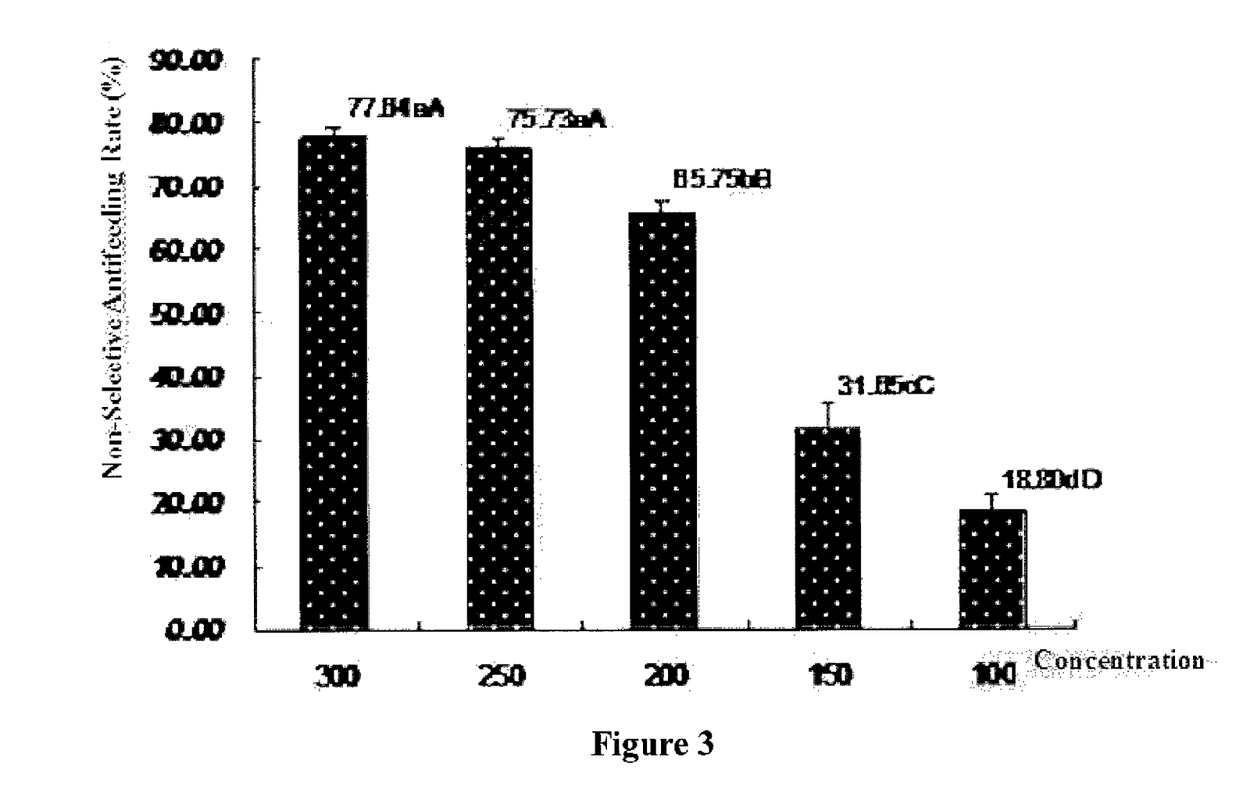
FIG. 3 shows non-selective antifeeding effects of N6-(2-hydroxyethyl)-adenosine on diamondback moth.

Forty-eight (48) hours after the treatment, the non-selective antifeeding rates of the larvae tested with 300 mg/L and 250 mg/L of N6-(2-hydroxyethyl)-adenosine (prepared using a 20% suspension) were 77.64% and 75.73%, respectively, indicating that there was no significant difference between the non-selective antifeeding rates of these two groups. However, the non-selective antifeeeding rates of both groups were notably higher than those of the groups treated with lower concentrations of the solutions (P<0.01).

Development Retardation Effects of N6-(2-Hydroxyethyl)-Adenosine on diamondback Moth After being treated with 300 mg/L, 250 mg/L, 200 mg/L, 150 mg/L and 100 mg/L of N6-(2-hydroxyethyl)-adenosine (prepared using a 20% suspension), the third-instar diamondback moth larvae showed symptoms, including reduced feeding, which were accompanied with reduced dejecta, sluggishness, and lack of energy. Three (3) days later, declining trends were observed in their weight gains. The decline trends became more significant with increasing concentrations of the treatment solutions (Table 5). The average weights gained by the tested larvae in various treatment groups were all notably lower than that of the control group ((P<0.01). From the results shown in Table 5, in can be determined that 3 days after treatments with 300 mg/L, 250 mg/L, 200 mg/L, 150 mg/L and 100 mg/L solutions, the growth inhibition rates of the third-instar larvae were 90.59%, 87.13%, 73.76%, 52.48% and 18.32%, respective. There was no significant difference between the weight gain inhibition rates of the 300 mg/L and 250 mg/L treatment groups. The rate of the 300 mg/L treatment group was significantly higher than that of any other treatment groups (P<0.01). The 250 mg/L treatment group had a weight gain inhibition rate that was significantly higher than that of the 200 mg/L treatment group (P<0.05) and remarkably higher than those of other groups treated with lower concentrations of the solutions (P<0.01). Significant differences could be seen among the weight gain inhibition rates of the 200 mg/L, 150 mg/L and 100 mg/L treatment groups ((P<0.01).

TABLE 5

Impact of the N6-(2-Hydroxyethyl)-Adenosine on the Growth and Development of Diamondback Moth

| Treatment Concentration (mg/L) | Average Weight (10 Tested Larvae) (mg) | | Weight Gain Inhibition Rate (%) |
|---|---|---|---|
| | Pre-Treatment | $\Delta_{4d}$ | |
| 300 | 5.58 | 0.48 eE | 90.59 aA |
| 250 | 5.55 | 0.65 eE | 87.13 aAB |
| 200 | 5.58 | 1.33 dD | 73.76 bB |
| 150 | 5.60 | 2.40 cC | 52.48 cC |
| 100 | 5.63 | 4.13 bB | 18.32 dD |
| CK | 5.55 | 5.05 aA | / |

Similar results were obtained from similar experiments carried out with Formulation Nos. 3-5, 7-10 (experimental data omitted).

DISCUSSIONS

Until now, only a few studies have been done on N6-(2-Hydroxyethyl)-Adenosine both at China and abroad, and the majority of the limited studies are focused on its medical use on human. Inventors of the present invention conducted a study on N6-(2-hydroxyethyl)-adenosine and found that it had a strong lethal effect on diamondback moth.

Inventors of the present invention came up with suspensions made with 20% N6-(2-hydroxyethyl)-adenosine during the research as a sample or embodiment. It is easily known that any concentration can optionally be used or selected. In order to explore its pathogenic effects on diamondback moth, we prepared N6-(2-hydroxyethyl)-adenosine solutions with different concentrations to test its stomach poisoning, antifeeding and growth inhibition effects on the moth. The test results obtained indicated that 96 hours after treatments with N6-(2-hydroxyethyl)-adenosine, the average corrected death rates of the third-instar diamondback moth larvae groups tested with 1000 mg/L and 800 mg/L solutions were 86.84% and 84.21%, respectively, indicating that there was no significant difference between them. However, these average corrected death rates were significantly higher than that of the 600 mg/L treatment group (P<0.05) and remarkably higher than those of the 400 mg/L and 200 mg/L treatment groups (P<0.01). These results can be used as guidance for field tests of the solution in terms of helping set the upper and lower levels of the active ingredient concentrations, for example to 1000 mg/L and 600 mg/L.

The tested larvae showed apparent declines in their feeding capacities after being treated with 300 mg/L, 250 mg/L, 200 mg/L, 150 mg/L and 100 mg/L of N6-(2-hydroxyethyl)-adenosine. Forty-eight (48) hours after the treatments, no significant difference was observed between the selective and non-selective antifeeding rates of the 300 mg/L and 250 mg/L test groups, even though both were remarkably significantly higher than those of the lower concentration treatment groups (P<0.01). The 200 mg/L treatment group had a selective and a non-selective antifeeding rates of 71.30% and 65.75%, respectively, 48 hour after the treatment, both of which were significantly higher than those of the 150 mg/L and 100 mg/L treatment groups (P<0.01), suggesting that even though the N6-(2-hydroxyethyl)-adenosine suspension had relatively low stomach poisoning effects on diamondback moth when its active ingredient contents were in the range from 200 mg/L to 300 mg/L, it was still able to inhibit the feeding activities of the moth. Therefore, this reagent can be used as a pest control measure on crops (e.g., vegetables) when dealing with small population of diamondback moths.

After treatments with N6-(2-hydroxyethyl)-adenosine, the third-instar diamondback moth larvae showed a declining trend in their weight gains. The growth inhibition rates of larvae groups tested with 300 mg/L, 250 mg/L, 200 mg/L, 150 mg/L and 100 mg/L solutions were 90.59%, 87.13%, 73.76%, 52.48% and 18.32%, respectively. No significant difference was found between the weight gain inhibition rates of the 300 mg/L and 250 mg/L treatment groups; however, the growth inhibition rates of these two groups were significantly higher than all other groups ($P<0.01$). The weight gain inhibition rate of the 250 mg/L treatment group was significantly higher than that of the 200 mg/L group ($P<0.05$) and significantly higher than any other group treated with lower concentrations of the solutions ($P<0.01$).

Diamondback moth needs incessant feeding in order to maintain its regular growth. Pesticides with high concentrations of N6-(2-hydroxyethyl)-adenosine can kill this moth fast, while low concentrations of N6-(2-hydroxyethyl)-adenosine are able to reduce its feeding activities, inhibit its growth, and eventually lead to death of the moth. Therefore, N6-(2-hydroxyethyl)-adenosine can be developed into a new and safe crop biopestide against diamondback moth.

Example 9

Roles of N6-(2-Hydroxyethyl)-Adenosine in the Insecticidal Activity of Aphids

We obtained results similar to those for the diamondback moth embodiments through our experiments and found that N6-(2-hydroxyethyl)-adenosine was also able to kill aphids, even though the lethal concentration in this case was different (experimental data omitted).

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims

What is claimed is:

1. A method for controlling a pest on a crop, comprising applying a pesticide that comprises N6-(2-hydroxyethyl)-adenosine as an active ingredient for controlling the pest.

2. The method according to claim 1, further comprising a dispersing agent as an auxiliary agent.

3. The method according to claim 1, further comprising an antifreeze agent or a thickening agent as an auxiliary agent.

4. The method according to claim 2, wherein the pesticide comprises 20 wt % N6-(2-hydroxyethyl)-adenosine, 1-3 wt % dispersing agent, and 66.5% wt % water.

5. The method according to claim 2, wherein the dispersing agent is one or more selected from sodium lignin sulfonate, NNO, Agricultural Emulsifier 500#, Agricultural Emulsifier 700#, Agricultural Emulsifier 600#, Agricultural Emulsifier 1602#, methylene bis-methylnaphthalene sodium sulfonate, sodium salt of alkyl naphthalene sulfonate condensate, or polyoxyethylene castor oil.

6. The method according to claim 2, wherein the dispersing agent comprises 3 wt % sodium lignin sulfonate, 2 wt % Agricultural Emulsifier 700#, 1~2 wt % Agricultural Emulsifier 600#, 2 wt % Agricultural Emulsifier 1602#, 1 wt % methylene bis-methylnaphthalene sodium sulfonate, 1 wt % sodium salt of alkyl naphthalene sulfonate condensate, or 1 wt % polyoxyethylene castor oil.

7. The method according to claim 2, wherein the dispersing agent comprises 3 wt % sodium lignin sulfonate or 1.5 wt % Agricultural Emulsifier 600#.

8. The method according to claim 1, wherein the pesticide exists in a form of a suspension concentrate, an emulsion in water, a suspoemulsion, a micro emulsion, a water dispersible granule, a dry flowable, a soluble granule, or a capsule suspension.

9. The method according to claim 3, wherein the thickening agent is one or more selected from carboxymethyl cellulose, urea, poly vinyl alcohol, aluminum magnesium silicate, or xanthan gum.

10. The method according to claim 3, wherein the antifreeze agent is one or more selected from ethylene glycol, propylene glycol, glycerol, glycerin-diethylene glycol diethyl ether, methyl-bis-propylene glycol, or urea.

11. The method according to claim 1, wherein the pest is one selected from lepidoptera, hymenoptera, or homoptera.

12. The method according to claim 1, wherein the pest is one selected from diamondback moth or aphid.

13. The method according to claim 1, wherein the pest is one selected from Lepidoptera or homoptera.

14. The method according to claim 1, wherein the pest is diamondback moth.

* * * * *